United States Patent
Sutovsky et al.

(10) Patent No.: US 7,368,249 B2
(45) Date of Patent: May 6, 2008

(54) METHODS AND COMPOSITIONS FOR EVALUATION AND MODULATION OF FERTILITY

(75) Inventors: Peter Sutovsky, Columbia, MO (US); Klaus van Leyen, Charlestown, MA (US)

(73) Assignees: The Curators of the University of Missouri, Columbia, MO (US); Slaon-Kettering Institute for Cancer Research, New York, NY (US)

( * ) Notice: Subject to any disclaimer, the term of this patent is extended or adjusted under 35 U.S.C. 154(b) by 239 days.

(21) Appl. No.: 10/898,141

(22) Filed: Jul. 23, 2004

(65) Prior Publication Data

US 2005/0112699 A1 May 26, 2005

Related U.S. Application Data

(60) Provisional application No. 60/489,871, filed on Jul. 24, 2003.

(51) Int. Cl.
*G01N 33/53* (2006.01)

(52) U.S. Cl. .................. 435/7.1; 435/7.2; 435/7.92; 436/517; 436/518

(58) Field of Classification Search ................ 435/7.1, 435/7.2, 7.92; 436/517, 518
See application file for complete search history.

(56) References Cited

U.S. PATENT DOCUMENTS

| | | | |
|---|---|---|---|
| 4,708,964 A | 11/1987 | Allen | 514/533 |
| 5,232,941 A | 8/1993 | Cho et al. | 514/445 |
| 5,310,959 A | 5/1994 | Shroot et al. | 554/69 |
| 5,326,785 A | 7/1994 | Cho et al. | 514/465 |
| 5,861,268 A | 1/1999 | Tang et al. | 435/25 |
| 5,928,654 A | 7/1999 | Duranton | 424/401 |
| 6,099,834 A | 8/2000 | Stanley | 424/94.1 |
| 6,217,875 B1 | 4/2001 | Murai et al. | 424/195.1 |
| 6,541,519 B2 | 4/2003 | Collin et al. | 514/558 |
| 6,586,181 B1 | 7/2003 | Fox et al. | 435/6 |
| 6,589,758 B1 | 7/2003 | Zhu | 435/15 |

OTHER PUBLICATIONS

Wells et al. Biochemistry (1990) vol. 29, p. 8509-8517.*
Ngo et al. The Protein Folding Problem and Tertiary Structure Prediction, (1995) Chapter 14, p. 433-506.*
Bork et al. Genome Research (2000) vol. 10, p. 398-400.*
Skolnick et al. Trends in Biotech. (2000) vol. 18, p. 34-39.*
Smith et al. Nature Biotechnology (1999) vol. 15: 1222-1223.*
Sutovsky et al. SSR 2002 Annual Meeting Abstract, Jul. 28-31, 2002 Baltimore, MD.*
U.S. Appl. No.10/778,942, filed Feb. 13, 2004, Sutovsky et al.
Brash, "Lipoxygenases: occurrence, functions, catalysts, and acquisition of substrate," *J. Biol. Chem.*, 274:23679, 1999.
Feussner and Wasternack, *Annu.* "The lipoxygenase pathway," *Rev. Plant Biol.*, 53:275, 2002.

Fritsch et al., "Selectivity of action of the lipoxygenase from rabbit reticulocytes on mitochondria and erythrocyte membranes" *Acta Biol. Med. Ger.*, 38(9):1315-1321, abstract, 1979.
Grüllich et al., "Inhibition of 15-lipoxygenase leads to delayed organelle degradation in the reticulocyte," *FEBS Lett.*, 489:51, 2001.
Lankin et al., "On the nature of the stimulation of the lipoxygenase from rabbit reticulocytes by biological membranes," *Biomed. Biochim Acta*, 44:655, 1985.
Lax et al., "Role of lipoxygenase in the mechanism of acrosome reaction in mammalian spermatozoa," *Biochim Biophys Acta*, 1043:12, 1990.
Lovercamp et al., "Arachidonate 15-lipoxygenase (15-LOX) in the sperm cytoplasmic droplet is a potential fertility marker in boars," Missouri Life Sciences Week 2004, Apr. 7, 2004.
Nakumura et al., "Enzyme immunoassays: heterogenous and homogenouse systems," In: *Handbook of Experimental Immunology* (4th Ed.), Weir et al. eds., 1:27, Blackwell Scientific Publ., Oxford, 1987.
Oliw and Sprecher, "Metabolism of polyunsaturated fatty acids by and (n-6)-lipoxygenase associated with human ejaculates," *Biochim Biophys Acta*, 1002:283, 1989.
Saez et al., "Pneumonia due to mycoplasma hominis in a health adult," *Scand. J. Infect. Dis.*, 35(4):282-284, 2003.
Schewe et al., "A lipoxygenase in rabbit reticulocytes which attacks phospholipids and intact mitochondria," *FEBS Lett.*, 60:149-152, 1975.
Sun and Funk, "Disruption of 12/15-lipoxygenase expression in peritoneal macrophages," *J. Biol. Chem.*, 271(39):24055-24062, 1996.
Sutovsky et al., "Degradation of paternal mitochondria after fertilization: implications for heteroplasmy, assisted reproductive technologies and mtDNA inheritance," *Reprod. Biomed. Online*, 8(1):24-34, 2004.
van Leyen et al., "A function for lipoxygenase in programmed organelle degradation," *Nature*, 395:392-395, 1998.
Yamamoto, "'Enzymatic' lipid peroxidation: reactions of mammalian lipoxygenases," *Free Radic Biol Med.*, 10:149-159, 1991.
Brener et al., "Remodeling of the Actin Cytoskeleton During Mammalian Sperm Capacitation and Acrosome Reaction", *Biology of Reproduction*, 68:837-845, 2003.
Dray, "Prostaglandins and reproduction. I. Physiological aspects" *Journal de gynecologie, obstetrique et biologie de la reproduction*, 20:7-17, 1991.
Foresta et al., "Male Fertility Is Linked to the Selenoprotein Phospholipid Hydroperoxide Glutathione Peroxidase", *Biology of Reproduction*, 67:967-971, 2002.
Sistina et al, "Arachidonic acid-induced acrosomal loss in the spermatozoa of a marsupial, the tammar wallaby (*Macropus eugenii*), " *Reprod. Fertil. Dev.*, 9:803-809, 1998.

* cited by examiner

*Primary Examiner*—Long V. Le
*Assistant Examiner*—Jacob Cheu
(74) *Attorney, Agent, or Firm*—Fulbright & Jaworski L.L.P.

(57) ABSTRACT

The present invention concerns compositions and methods for regulating or determining fertility in humans and animals. In various embodiments of the invention, LOX and other related enzymes can be used as fertility markers, contraceptive agents, or means of treating infertility. LOX may be detected in accordance with the invention in vitro or in vivo.

20 Claims, 8 Drawing Sheets

| Boar | Percoll fraction | Normal | PCD | DCD | Other |
|---|---|---|---|---|---|
| 17-2 | Immotile spermatozoa | 69.30% | 11.90% | 12.40% | 6.40% |
| 17-2 | Motile spermatozoa | 92.50% | 3.50% | 18% | 5.00% |
| 96-1 | Immotile spermatozoa | 44.50% | 32.50% | 18.00% | 5.00% |
| 96-1 | Motile spermatozoa | 97.50% | 1.00% | 1.00% | 0.50% |

FIG. 6

METHODS AND COMPOSITIONS FOR EVALUATION AND MODULATION OF FERTILITY

This application claims the priority of U.S. Provisional Patent Application Ser. No. 60/489,871, filed Jul. 24, 2003, the entire disclosure of which is specifically incorporated herein by reference.

The government may own rights in the present invention pursuant to grant numbers 99-35203 and 2002-02069 from the USDA.

BACKGROUND OF THE INVENTION

A. Field of the Invention

The present invention relates generally to the field of biology. More particularly, it concerns compounds associated with fertility and methods of use thereof.

B. Description of Related Art

Cytoplasmic droplets are remnants of spermiogenesis that often contain cytoplasm, mitochondria, and the Golgi complex. They are approximately 2 μm in size and are located on the midpiece of the spermatozoon in either the upper half or lower half of the midpiece, the proximal and distal positions, respectively. Cytoplasmic droplets (CD) are the most common abnormality associated with boar spermatozoa and it is recommended that ejaculates with more than 15% spermatozoa with CD should be discarded (Althouse, 1998).

Lipoxygenases (LOX) are enzymes that are ubiquitous in plants and animals and are member of a large family of dioxygenases (Brash, 1999; Feussner and Wasternack, 2002). The animal LOXs, mainly 5-LOX, 12-LOX, and 15-LOX, can peroxidate arachidonic acid at carbon-5, carbon-12, or carbon-15, respectively, as well as related polyunsaturated fatty acids like linoleic acid (Yamamoto, 1991).

15-Lipoxygenase was discovered in the rabbit reticulocyte in 1975 and found to directly attack phospholipids and peroxidate mitochondrial lipids (Schewe et al., 1975; Grüllich et al., 2001). Reticulocyte LOX is capable of degrading lipid membranes (Fritsch et al., 1979; Lankin et al., 1985). The reticulocyte LOX, 15-LOX, is a major pathway for organelle degradation in rabbit reticulocytes (Grüllich et al., 2001). In the presence of a LOX inhibitor, endoplasmic reticulum membranes incubated with 15-LOX in vitro were not permeabilized, but in the absence of the inhibitor permeabilization of endoplasmic reticulum membranes occurred (van Leyen et al., 1998).

Mitochondrial degradation in maturing reticulocytes was able to occur in the absence of ETYA (5,8,11,14-eicosatetraynoic acid), a LOX inhibitor, but was delayed in the presence of ETYA, indicating that LOX is largely responsible for the degradation of reticulocyte mitochondria.

Acrosomal exocytosis (AE), which is the exocytosis of soluble acrosome material after the fusion of the outer acrosomal membrane and overlying plasma membrane, is required for fusion of the spermatozoon with the plasma membrane (Lax et al., 1990). 15-LOX induces the acrosome reaction in the presence of $Ca^{2+}$ (Oliw and Sprecher, 1989; Lax et al., 1990).

Current methods of contraception include surgical sterilization of women and oral contraceptive use by women, which are the most common methods of contraception in the U.S. Hormone modulating contraceptives include combined (estrogen/progestin) contraceptives, such as combined injectable contraceptives, combined oral contraceptives; and progestin-only contraceptives, such as norplant implants, progestin-only injectable contraceptives, or progestin-only pills. However, combined estrogen/progestin oral contraceptives may cause or lead to thromboembolic disorders, cerebrovascular accidents, coronary artery disease, liver abnormalities, estrogen dependent cancers, and pregnancy. Other methods of contraception include intrauterine devices; cervical cap; barrier methods, such as male condoms, female condoms, diaphragms, spermicides, or contraceptive sponge; and rhythm methods, which are highly dependent on the individuals involved. Many of these methods may have far reaching side effects physiologically and otherwise. Thus, there is a need for improved methods of regulating fertility as well as methods for diagnosing fertility for both humans and a variety of animals.

SUMMARY OF THE INVENTION

In one aspect, the invention provides a method of evaluating the fertility of a sample of spermatozoa comprising detecting the content and/or activity of LOX in the sample, wherein an increased content and/or activity of LOX relative to a control sample is associated with decreased fertility. In the method, detecting the content and/or activity of LOX may comprise evaluating testicular, epididymal, and ejaculated spermatozoa. The sample may be semen. In certain embodiments of the invention, detecting may be by immunocytochemistry and/or electron microscopy utilizing colloidal gold particles, by Western blot analysis. In certain further embodiments the sample of spermatozoa is from a head of cattle, pig, goat, sheep, horse, pig, dog, cat or human. In one embodiment LOX is 12/15-LOX, which is also known as 15-LOX-1 or 15-LO. Detecting may comprise, for example, immunologic detection, detection with polyclonal antisera, detection with a monoclonal antibody preparation, ELISA, RIA, Western blot, detection of mRNA and/or detecting a product and/or substrate of LOX. Examples of detecting a product and/or substrate of LOX include HETE, HPETE and/or TBARS. In the method, detecting may comprise use of a sandwich ELISA comprising binding of LOX to a first antibody preparation fixed to a substrate and a second antibody preparation labeled with an enzyme, including alkaline phosphatase or horseradish peroxidase.

In another aspect, the invention provides a method of evaluating fertility of a subject, wherein a sample of spermatozoa is obtained from the subject, and wherein the results of the detecting LOX and/or activity thereof are correlated to the fertility of the subject. The method may further comprise detecting the content and/or activity of LOX in at least two samples of spermatozoa from the subject. A method of the invention may still further be defined as comprising evaluating fertility of a plurality of samples of spermatozoa and detecting the content and/or activity of LOX in the samples. A method of the invention may also still further comprise selecting at least one sample of spermatozoa from the plurality of samples based on the results of said detecting.

In yet another aspect, the invention provides a method of treating infertility in a mammal comprising decreasing LOX activity of spermatozoa. LOX activity may be decreased by any method, including in vitro or in vivo, and using antibodies that bind and inhibit LOX enzyme activity, depleting LOX from semen and contacting spermatozoa with an inhibitor that inhibits LOX activity. An inhibitor may be comprised in a pharmaceutically acceptable formulation.

In still yet another aspect, the invention provides a method of contraception in a mammal comprising increasing LOX enzyme activity of spermatozoa. Such a method may, in certain embodiments, comprise administering HPETE to the mammal and/or spermatozoa therefrom.

In still yet another aspect, the invention provides a method of in vitro fertilization and/or artificial insemination comprising: (a) screening at least one sample of spermatozoa for LOX content and/or activity; and (b) selecting a sample of spermatozoa for in vitro fertilization and/or artificial insemination based on said screening, wherein increased LOX content and/or activity relative to a control subject is associated with decreased fertility.

In still yet another aspect, the invention provides a method of in vitro fertilization and/or artificial insemination comprising: (a) obtaining a sample of spermatozoa; (b) decreasing LOX activity and/ content in the sample of spermatozoa; and (c) carrying out in vitro fertilization and/or artificial insemination with the sample.

In still yet another aspect, the invention provides a method of contraception comprising increasing LOX content and/or activity in spermatozoa of a subject. In any method of the invention, LOX may be 12/15-LOX. It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6 illustrates an example of the analysis of ejaculated spermatozoa from two boars, 17-2 and 96-1. The ejaculated spermatozoa were separated into three different fractions, a cellular debris fraction, an immotile spermatozoa fraction, and a motile spermatozoa fraction. The morphology of 100 spermatozoa was assessed and the percentages of each category, spermatozoa with normal morphology (Normal), spermatozoa with proximal cytoplasmic droplets (PCD), spermatozoa with distal cytoplasmic droplets (DCD), and spermatozoa with abnormalities other than cytoplasmic droplets (Other), were recorded.

DESCRIPTION OF ILLUSTRATIVE EMBODIMENTS

Figures 1A, 1B, 1C, 1D:
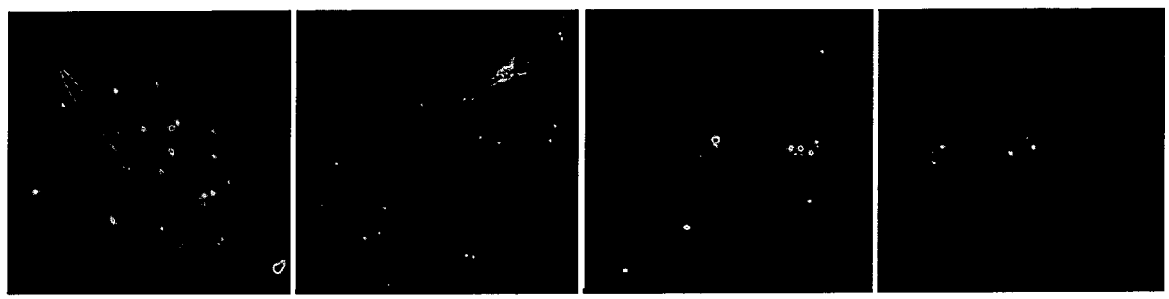
FIGS. 1A-1D illustrate an example of the residual bodies of spermatozoa from the testis (FIG. 1A), caput epididymis (FIG. 1B), corpus epididymis (FIG. 1C), and cauda epididymis (FIG. 1D) that were immunoreacted with anti-15-LOX antibody raised against a peptide from rabbit reticulocyte 15-LOX.

The invention overcomes the limitations of the prior art by providing novel methods and compositions for the detection of infertility as well as for the modulation of fertility both as a contraceptive and for increasing fertility. As described above, there is a need for improved methods of regulating fertilization, evaluating fertility, or diagnosing infertility. The invention therefore provides methods of ascertaining fertility of a sample of spermatozoa, as well as a subject, by detecting the presence and/or activity of LOX and LOX associated enzymes including 12/15-LOX. An elevation of LOX presence and/or activity in association with a sample of spermatozoa has been shown by the inventors to correlate with decreased fertility. Such LOX levels may be placed into context as elevated or not elevated by comparison to one or more control sample or as baseline created for a population of subjects. A LOX-associated enzyme refers to components of the ubiquitin-proteasome pathway which may facilitate the degradation of cytoplasmic droplets in conjunction with the LOX pathway. The ubiquitin-proteasome pathway is described, for example, in U.S. Provisional Patent App. Ser. No. 60/447,675, filed Feb. 14, 2003, the disclosure of which is specifically incorporated herein by reference.

In accordance with the results of such aspects, various interventions may be taken, such as therapies to increase fertility or selection or non-selection of a given sample of spermatozoa for fertilization in vitro or in vivo. The invention also provides, in certain embodiments, fertility regulating compositions and related methods. The invention includes use of inhibitors or binding agents for LOX enzymes for the regulation of fertility. Fertility may be modulated in accordance with the invention both in vivo and in vitro.

In various embodiments of the invention, contraceptive methods include administration of LOX and/or upregulation of LOX activity in association with spermatozoa. As used herein, "contraceptive" means an agent that when administered deliberately prevents or inhibits conception or pregnancy, either directly or indirectly. Similarly, as used herein, "contraception" means the deliberate prevention of conception or pregnancy, either directly or indirectly.

The current invention relates to the finding that an increase in the presence of lipoxygenase (LOX) within semen or spermatozoa is associated with decreased fertility. As the formation of spermatozoa in mammals is highly conserved, the invention may find use with a number of species. This is further indicated by the finding of LOX accumulation in the sperm of male mice, bulls, boar and stallions. The current invention may therefore find use with potentially any mammal including, for example, beef and dairy cattle, pigs, horses, cats, dogs, primates and specifically humans. 12/15-LOX enzymes from mammals are well known to those of skill in the art and may be detected or modulated in accordance with the invention using standard methodology.

As indicated above, the inventors have found the presence of large amounts of LOX to associate with reduced fertility in boars. The inventors have further identified the location of LOX in association with the cytoplasmic droplet (CD) of spermatozoa to correlate with infertility. The removal of the sperm cytoplasmic droplet (CD) in the epididymis puts the final touch on the morphogenesis of a mammalian spermatozoon. The cytoplasmic droplet disintegrates as it is removed from the sperm tail connecting piece, to be subsequently phagocytosed by the clear cells of the caput-epididymal epithelium. The inventors have shown that 12/15-lipoxygenases (12/15-LOX) and related enzymes are capable of peroxidizing the intracellular membrane structures, and accumulate in the sperm of male mice, bulls, boar and stallions. Various antibodies against lipoxygenase recognize antigens in the cytoplasmic droplets of epididymal and ejaculated bull and boar spermatozoa. Using such probes, several boars with a high percentage of CD retention in ejaculated sperm were identified. In these boars, repeated, bi-weekly ejaculation reduced the percentage of spermatozoa with retained cytoplasmic droplets. While some degree of CD relocation (from proximal to distal CD-position) and removal was observed during epididymal passage, most cauda-epididymal spermatozoa still had intact distal droplets. The LOX pathway was therefore shown to be involved in the removal and degradation of sperm cytoplasmic droplets, the retention of which has been shown to cause infertility in humans and animals.

In a further study, semen samples of 17 boars were screened for LOX using western blotting technique. A strong negative correlation was found between the relative density of the LOX-protein band and boar fertility, when protein load for western blotting was standardized. The association with increased LOX and infertility was thus demonstrated.

The findings of the inventors have important diagnostic and therapeutic applications. Novel methods are needed for diagnosing and treating infertility. By detection of infertility, one or more interventions may be taken. New methods of contraception are further needed in view of the shortcomings of the methods currently available.

I. Diagnostic Assays

In accordance with one aspect of the invention, methods are provided for assaying fertility by detecting for the presence of a LOX enzyme and/or activity thereof in association with spermatozoa samples. As is known to those of skill in the art, the detection of the presence of a given enzyme such as LOX need not be carried out on the enzyme itself, and may be carried out, for example, on one or more product catalyzed by the enzyme. Thus when detection of LOX is referred to herein, this includes indirect detection of precursors and/or products of LOX. Examples of such compounds that may be detected to show the presence of LOX include products hydroxyeicosatetraenoic acids (HETEs), as well as hydroperoxyeicosatetraenoic acids (HPETEs), which are catalyzed by the reaction LOX with arachidonic acid. Kits for detection of various HETEs and/or HPETEs are commercially available, for example, from Cayman Chemical or Assay Designs, Inc., both of Ann Arbor, Mich. Further down stream products including thiobarbiturate-reactive substances (TBARS) may also be detected. Commercial kits for detection of TBARS are also known. Many assay formats for detecting the presence and/or activity of enzymes such as LOX are well known to those of skill in the art and may be used in accordance with the invention. Such assays may be qualitative or quantitative. Examples of some of these are described below for illustrative purposes.

A. Immunologic Detection of LOX

One aspect of the present invention entails the use of antibodies in the immunologic detection of LOX. Various useful immunodetection methods have been described in the scientific literature, such as, e.g., Nakamura et al. (1987; incorporated herein by reference). Immunoassays in their most simple and direct sense are binding assays. Certain preferred immunoassays are the various types of enzyme linked immunosorbent assays (ELISAs) and radioimmunoassays (RIA). Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Such a sample will generally contain spermatozoa of a subject being analyzed, for example, semen.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with LOX. After this time, the LOX-antibody mixture will be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Usually, the primary immune complexes may be detected by means of a second binding ligand that has binding affinity for the LOX or the LOX-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the LOX or anti-LOX antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

B. ELISA

As a part of the practice of the present invention, the principles of an enzyme-linked immunoassay (ELISA) may be used. ELISA was first introduced by Engvall and Perlmann (1971) and has become a powerful analytical tool using a variety of protocols (Engvall, 1980; Engvall, 1976; Engvall, 1977; Gripenberg et al., 1978; Makler et al., 1981; Sarngadharan et al., 1984). ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995 incorporated herein by reference).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In one embodiment, the invention provides a "sandwich" ELISA, where anti-LOX antibodies are immobilized onto a selected surface, such as a well in a polystyrene microtiter plate or a dipstick. Then, a test composition suspected of containing LOX, e.g., a clinical sample, is contacted with the surface. After binding and washing to remove non-specifically bound immunocomplexes, the bound antigen may be detected by a second antibody to the LOX.

In another exemplary ELISA, polypeptides from the sample are immobilized onto a surface and then contacted with the anti-LOX antibodies. After binding and washing to remove non-specifically bound immune complexes, the bound antibody is detected. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the LOX are immobilized involves the use of antibody competition in the detection. In this ELISA, labeled antibodies are added to the wells, allowed to bind to the LOX, and detected by means of their label. The amount of LOX in a sample is determined by mixing the sample with the labeled antibodies before or during incubation with coated wells. The presence of LOX in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 h to 2 h to 4 h, at temperatures preferably on the order of 25° C. to 27° C., or may be overnight at about 4° C. or so.

To provide a detecting means, the second or third antibody will have an associated label to allow detection. Commonly, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analytes.

C. Immunohistochemistry

While primarily useful in research contexts, immunohistochemistry may be useful according to the present invention in identifying LOX. This may involve testing of both fresh-frozen and formalin-fixed, paraffin-embedded tissue blocks prepared for study by immunohistochemistry (IHC). For example, tissue sections from testis and epididymis can be fixed and embedded in paraffin. The paraffinized tissue sections can then be cut into sections and placed on slides. The presence of LOX in the tissue sections can then be assessed by the immunodetection methods described herein.

D. Immunodetection Kits

In further embodiments, the invention provides immunological kits for use in detecting LOX in biological samples. Such kits will generally comprise one or more LOX or LOX-binding proteins that have immunospecificity for various LOX and for antibodies. More specifically, the immunodetection kits will thus comprise, in suitable container means, one or more LOX, antibodies that bind to LOX, and antibodies that bind to other antibodies via Fc portions.

In certain embodiments, the LOX or primary anti-LOX antibody may be provided bound to a solid support, such as a column matrix or well of a microtitre plate. Alternatively, the support may be provided as a separate element of the kit.

The immunodetection reagents of the kit may include detectable labels that are associated with, or linked to, the given antibody or LOX itself. Detectable labels that are associated with or attached to a secondary binding ligand are also contemplated. Such detectable labels include chemilluminescent or fluorescent molecules (rhodamine, fluorescein, green fluorescent protein, luciferase, radiolabels ($^3$H, $^{35}$S, $^{32}$P, 14C, $^{131}$I) or enzymes (alkaline phosphatase, horseradish peroxidase).

The kits may further comprise suitable standards of predetermined amounts, including both antibodies and LOX. These may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, LOX and any other reagent containers in close confinement for commercial sale. Such containers may include injection or blow-molded plastic containers into which the desired vials are retained.

II. Modulators of Lipoxygenase and Pharmaceutical Compositions

The present invention involves, in certain aspects, the use of one or more modulators of LOX for the manipulation of fertility in a subject or a sample of semen. In accordance with the invention, an increase of LOX and/or LOX activity in a sample of spermatozoa may be induced in order to achieve contraception, whereas administration of a LOX inhibitor to a sample of spermatozoa may be used to increase fertility of the sample. Generally it is understood that an inhibitor of an enzyme is capable of selectively inhibiting the given enzyme.

Many LOX inhibitors are known to those of skill in the art and may find use with the invention. Inhibitors of LOX include, but are not limited to, baicalein (see Sekiya and Okuda, et al., 1982; Kimura et al., 1987; Kubo et al., 1987; see U.S. Pat. Nos. 5,861,268; 6,589,758), caffeic acid (see Koshihara et al., 1984; Shureiqi et al, 2000; see U.S. Pat. Nos. 5,232,941; 5,326,785), CDC (see Cho et al., 1991; see U.S. Pat. No. 5,861,268), ETI (Salari et al., 1984; Omina and Hammarström et al., 1980; Hammarström, 1977; see U.S. Pat. No. 5,310,959), ETYA (see Hammarström, 1977; Kliewer, et al., 1995; see U.S. Pat. Nos. 4,708,964; 5,928,654; 6,541,519), and NDGA (see Salari et al., 1984; Hope et al., 1983; see U.S. Pat. Nos. 6,099,834; 6,217,875; 6,486,181).

Modulators which upregulate LOX may also find use in accordance with the invention. One example of such a known upregulator of LOX is hydroperoxyeicosatetraenoic acid (e.g., 15-HPETE). This compound is commercially available for example, from Biomol Research Laboratories. Therefore, upregulation of LOX may be achieved by use of HPETE.

In certain embodiments of the invention, a LOX modulator may be administered in vivo, either systemically or locally; as well as in vitro, in a pharmaceutical formulation. Pharmaceutical aqueous compositions of the present invention will generally comprise an effective amount of one or more LOX enzyme modulators dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to a human, unless specifically designed to elicit such a response. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The actual dosage amount of a composition of the present invention administered to a subject can be determined by physical and physiological factors such as body weight and on the route of administration. With these considerations in mind, the dosage of a peptide, polypeptide, polynucleotide, or LOX inhibitor composition for a particular subject and/or course of treatment can readily be determined.

The compositions of the present invention can be administered intravenously, intradermally, intraarterially, intraperitoneally, intraarticularly, intrapleurally, intratracheally, intranasally, intravaginally, topically, intramuscularly, intraperitoneally, subcutaneously, intravesicularlly, mucosally, orally, topically, locally using aerosol, injection, infusion, continuous infusion, localized profusion bathing target cells directly or via a catheter or lavage. Typically, such compositions are prepared as injectables, either as liquid solutions or suspensions; solid forms suitable for preparing solutions or suspensions upon the addition of a liquid prior to injection can also be prepared; and the preparations can also be emulsified. The compositions will be sterile, a fluid to the extent that easy syringability exists, stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

Although it is most preferred that compositions of the present invention be prepared in sterile water containing other non-active ingredients, made suitable for injection, solutions of such active ingredients can also be prepared in water suitably mixed with a surfactant, such as hydroxypropylcellulose, if desired. Dispersions can also be prepared in liquid polyethylene glycol and mixtures thereof, and in oils. The carrier can also be a solvent or dispersion medium containing, for example, water, ethanol, polyol (for example, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is effective for effecting fertility, including a contraceptive effect. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

While LOX modulators are known to those of skill in the art, methods may further be employed for the identification of additional modulators. In one aspect, this and/or the evaluation of a given treatment may be done using in vivo or in vitro assays. In vivo assays involve the use of various animal models, including transgenic animals that have been engineered to have specific defects, or carry markers that can be used to measure the ability of a candidate substance to reach and affect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, survival), or instead a broader indication such as behavior, anemia, immune response, etc. A technique for high throughput screening of compounds is described in WO 84/03564. Large numbers of small peptide test compounds are synthesized on a solid substrate, such as plastic pins or some other surface. Bound polypeptide is detected by various methods.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

To identify a LOX modulator generally, one will determine the function of LOX activity in the presence and absence of the candidate substance, a modulator defined as any substance that alters function. For example, a method generally comprises: providing a candidate modulator; admixing the candidate modulator with an isolated compound or cell, or a suitable experimental animal; measuring one or more characteristics of the compound, cell or animal in the prior step; and comparing the characteristic measured in the previous step with the characteristic of the compound, cell or animal in the absence of said candidate modulator, wherein a difference between the measured characteristics indicates that said candidate modulator is, indeed, a modulator of the compound, cell or animal. Assays may be conducted in cell free systems, in isolated cells, or in organisms.

III. Generating Antibodies Reactive with LOX

In another aspect, the present invention contemplates an antibody that binds immunologically with a LOX molecule, or any portion thereof. An antibody can be a polyclonal or a monoclonal antibody composition. Means for preparing and characterizing antibodies are well known in the art (see, e.g., Harlow and Lane, 1988).

LOX sequences are well known from many species and may be used for the production of antibodies (see, e.g., reviews by Brash (1999) and Conrad (1999). LOX sequences, are also generally conserved among mammals, and are commonly cross reactive between species. Particular useful for production of LOX antibodies are the C-termini of LOX sequences. Non-limiting examples of C-termini that may be used to raise LOX antibodies include sequences from rabbit reticulocyte LOX (YLRPSIVENSVAI (SEQ ID NO:1)); human 15-LOX-1 (YLRPSVVENSVAI (SEQ ID NO:2)); human 15-LOX-2 (YLDPPLIENSVSI (SEQ ID NO:3)); human 12-LOX-P (YLKPSCIENSVTI (SEQ ID NO:4)); human 12-(R)-LOX (YLDPVLIENSISI (SEQ ID NO:5)); human 5-LOX (YLSPDRIPNSVAI (SEQ ID NO:6)); mouse 12-LOX-L (YLRPSLVENSVAI (SEQ ID NO:7); mouse 12-LOX-P (YLKPSRIENSITI (SEQ ID NO:8)); mouse 12-LOX-E (YLRPSLVENSVTI (SEQ ID NO:9)); mouse 15-LOX T.2 (YLDPPLIENSVSI (SEQ ID NO:10), Genbank accession XP_203460); rat 12-LOX (YLRPSMVENSVAI (SEQ ID NO:11) Genbank accessions 152462, Q02759, S30051); rat 15-LOX T.2 (YLDPPLIENSVSI (SEQ ID NO:12), Genbank accession AF415240.1); rat 5-LOX (YLSPDRIPNSVAI (SEQ ID NO:13), Genbank accession P12527); rat 5-LOX (YLSPDRFQTV (SEQ ID NO:14), Genbank accessions NP_036954, AAA41538); bovine 12-LOX (YLRPSLVENSVAI (SEQ ID NO:15)); bovine 15-LOX-2 (YLDPPLIENSVSI (SEQ ID NO:16)); and pig 12-LOX (YLRPSRVENSVAI (SEQ ID NO: 17), or YLRPSSVENSVAI (SEQ ID NO: 18)).

A polyclonal antibody is generally prepared by immunizing an animal with an immunogen comprising a peptide or polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of LOX can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

Monoclonal antibodies may find use with the invention in standard immunochemical procedures, such as ELISA and Western blot methods and in immunohistochemical procedures such as tissue staining, as well as in other procedures which may utilize antibodies specific to LOX-related antigen epitopes. Additionally, it is proposed that monoclonal antibodies specific to the particular LOX of different species may be utilized in other useful applications.

In general, both polyclonal and monoclonal antibodies against LOX may be used in a variety of embodiments. For example, they may be employed in diagnostic as well as therapeutic applications. They may also be used in inhibition studies to analyze the effects of LOX related peptides in cells or animals. Anti-LOX antibodies will also be useful in immunolocalization studies to analyze the distribution of LOX polypeptides, for example, during maturation of spermatozoa. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified LOX. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Purification and Detection of LOX or Activity Thereof

In certain aspects of the invention, techniques may be used for the isolation or removal of LOX or antigens thereof from a sample. For example, LOX may be isolated for further use as well as for generation of one or more diagnostic reagents. One or more purification techniques may also find use in accordance with the invention for the improvement of semen sample quality by way of reduction of LOX content.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of a protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of LOX, or assessing the amount of LOX polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number" (i.e., 2-fold, 5-fold, 10-fold, 50-fold, 100-fold, 1000-fold, etc.). The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE and according to how extensively it is glycosylated (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

V. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Evaluation of Boar Spermatozoa Shows 15-LOX Localization in Cytoplasmic Droplets A study was initiated to determine the role that 15-LOX plays in organelle degradation in the cytoplasmic droplet (CD) of boar spermatozoa, and further to determine whether boar spermatozoa contains 15-LOX. Testicular and epididymal spermatozoa from boars that had CD in their ejaculates were examined for the presence of 15-LOX using immunocytochemistry. It was found that the residual body of differentiating spermatids in the testis had strong labeling of 15-LOX (FIG. 1A). There was strong 15-LOX labeling in the CD of spermatozoa in the caput epididymis, with weak labeling of 15-LOX in the connecting piece (FIG. 1B). Spermatozoa displayed 15-LOX labeling in the CD and connecting piece of corpus epididymal spermatozoa (FIG. 1C) and cauda epididymal spermatozoa (FIG. ID). Spermatozoa that retained the CD through ejaculation were found to have strong 15-LOX labeling in the CD. The expression of 15-LOX and its retention in the sperm CD is conserved as it was also detected in the African wild babirusa boar (*Babyrousa babyrussa*), human, stallion, and mouse testicular and epididymal spermatazoa.

Figures 2A, 2B, 2C:
FIGS. 2A-2C illustrate that 15-LOX is localized in the CD of the mammalian spermatozoa. Spermatozoa from the corpus epididymis were immunoreacted to an anti-15-LOX antibody that was conjugated to 12 nm colloidal gold particles. The particles (see arrows in FIG. 2A) are present mainly within the cytoplasmic droplet on the midpiece of the boar epididymal spermatozoa.

A study was conducted to localize the 15-LOX within spermatozoa. Boar spermatozoa pellets were incubated with 15-LOX conjugated to 12 nm colloidal gold particles and processed for electron microscopy. FIG. 2 is a representative picture of the localization of 15-LOX in the CD of the epididymal spermatozoa. Colloidal gold particles were mostly located on the inner region of the plasma membrane but some particles may also be found scattered throughout the CD.

Example 2

15-LOX is Present in Testicular, Epididymal, and Ejaculated Spermatozoa

Figures 3A, 3B, 3C, 3D:
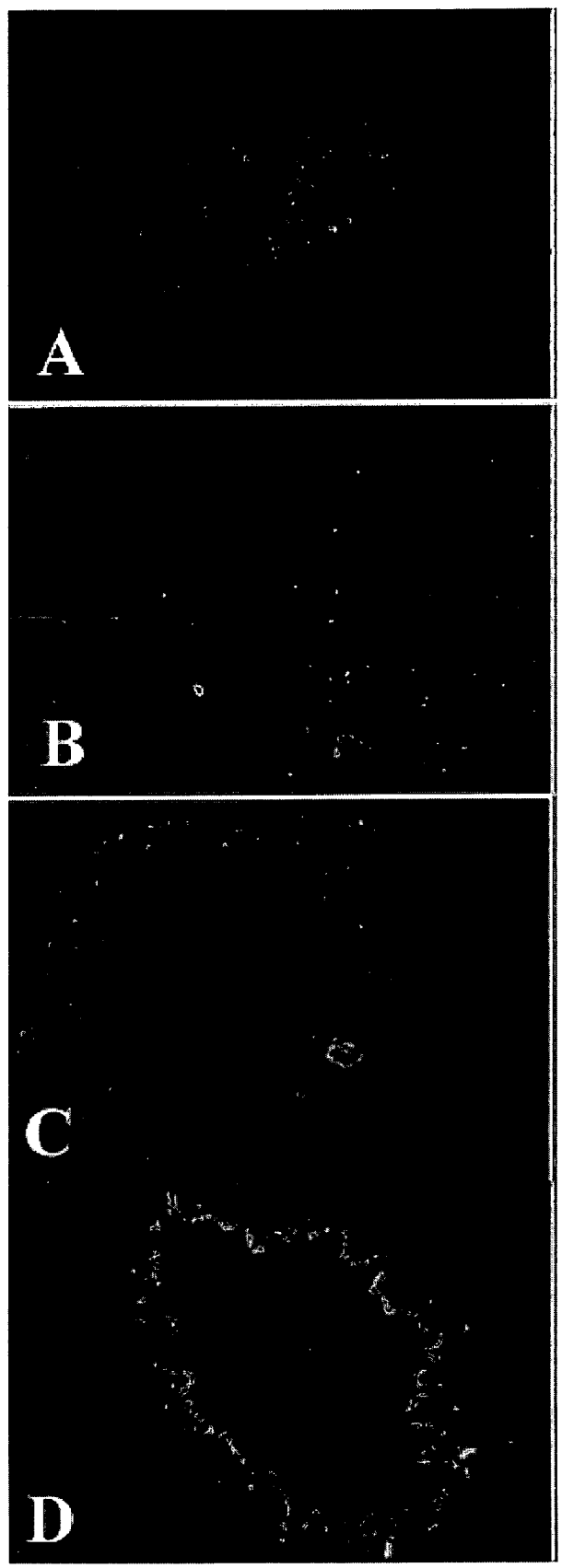
FIGS. 3A-3D illustrate an example of anti-15-LOX antibody incubated with the spermatogenic cells within tissue sections from the testis (FIG. 3A), caput epididymis (FIG. 3B), corpus epididymis (FIG. 3C), and cauda epididymis (FIG. 3D).

Taking into account the detection of 15-LOX in the CD of boar spermatozoa, it was decided to determine the presence of 15-LOX in different tissue sections of boar spermatozoa. Testicular and epididymal tissue sections from a boar with a high incidence (an average of 49.8% in five collections) of abnormal spermatozoa in ejaculate were analyzed for the presence of 15-LOX using immunocytochemistry. The residual body in the testicular tissue was found to be strongly crossreactive with 15-LOX (FIG. 3A). All three compartments of the epididymis, the caput, corpus, and cauda, were crossreactive with 15-LOX in the epididysomes (FIGS. 3B, 3C, and 3D, respectively), which are protein-rich vesicles that are present in the epididymal lumen (reviewed by Saez et al., 2003).

Figure 4:
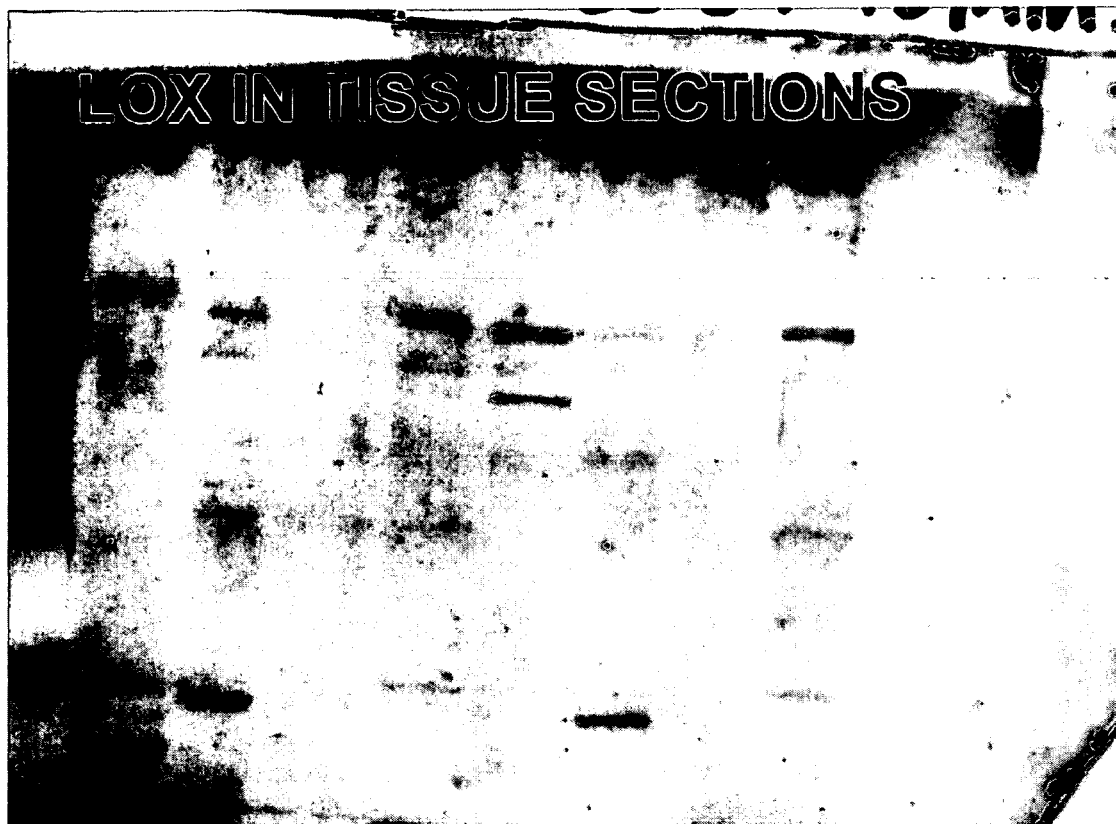
FIG. 4 illustrates an example of Western blot analysis for the presence of 15-LOX in spermatozoa isolated from testis and epididymis of a boar. Known molecular weight proteins were used as a marker (lane 1). Analysis of the left side of the reproductive tract includes left testis sperm (lane 2), left caput sperm (lane 3), left corpus sperm (lane 4), and left cauda sperm (lane 5). Analysis of the right side of the reproductive tract include right testis sperm (lane 6), right caput sperm (lane 7), right corpus sperm (lane 8), and right cauda sperm (lane 9).

Spermatozoa from the testis and epididymis from the left and right side of the reproductive tract were incubated with 15-LOX and analyzed using Western blot analysis. The left testis showed different molecular weight bands than the right testis (FIG. 4). The right testis had two distinct bands at approximately 70-85 kDa while these bands were not present in the left testis. Spermatozoa in the left caput epididymis had two bands in the 70-85 kDa range that the right caput epididymis did not have, but both sides of the reproductive tract had spermatozoa with a crossreactive band at 30-35 kDa. Spermatozoa from the left and right corpus epididymis did not crossreact with 15-LOX. Spermatozoa from the left and right cauda epididymis had similar molecular weight bands. These bands appeared in the 70-85 kDa and 30-35 kDa range.

Example 3

Figure 5:
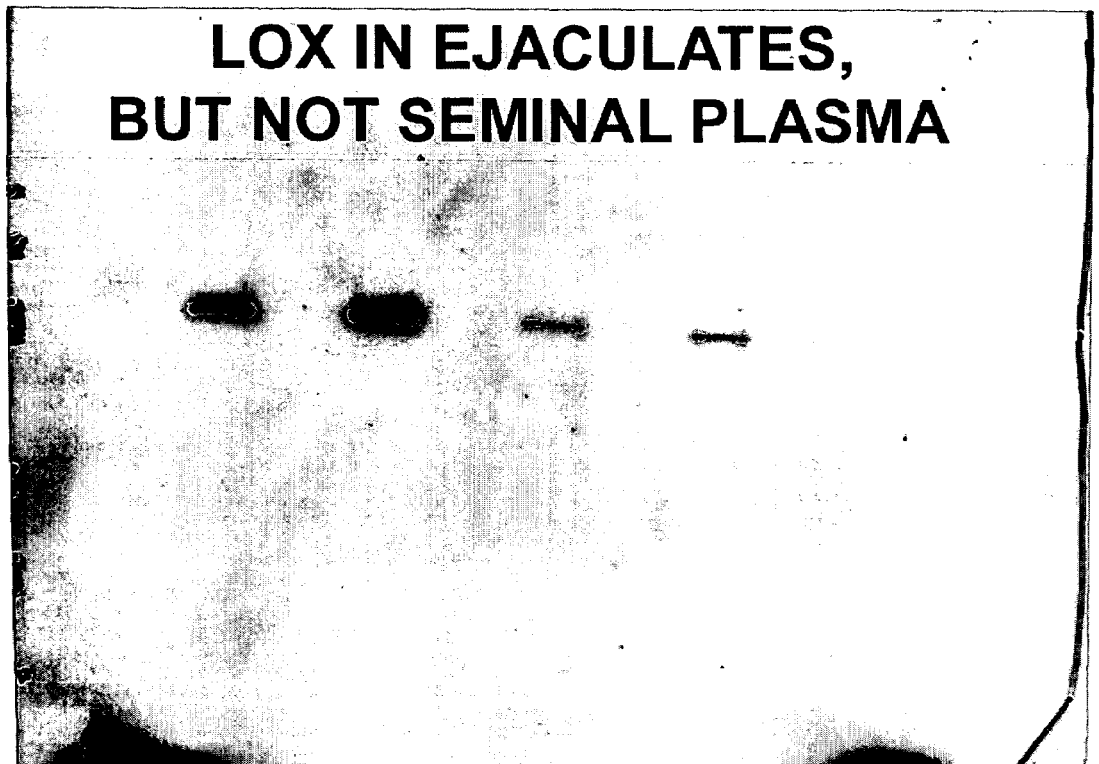
FIG. 5 illustrates an example of Western blot analysis for the presence of 15-LOX in seminal plasma and ejaculated spermatozoa centrifuged at different g-forces. It shows that LOX in boar semen is associated primarily with spermatozoa and not with seminal plasma. Known molecular weight proteins were used as a marker (lane 1). Analysis of boar 17-2 include sperm centrifuged at 1000×g (lane 2), seminal plasma centrifuged at 1000×g (lane 3), sperm centrifuged at 2500×g (lane 4), and seminal plasma centrifuged at 2500×g (lane 5). Analysis of boar 96-1 include sperm centrifuged at 1000×g (lane 6), seminal plasma centrifuged at 1000×g (lane 7), sperm centrifuged at 2500×g (lane 8), and seminal plasma centrifuged at 2500×g (lane 9).

Western Blot Analysis Shows Differential 15-LOX Crossreactivity in Different Boars and Different Samples from the Same Boar With varying levels of 15-LOX detected in different tissue sections of a single boar, it was decided to determine whether different boars, as well as different samples from a single boar, have varying levels of 15-LOX. Ejaculated spermatozoa from two boars, boar 17-2 and 96-1, were spun at either 1000×g or 2500×g and the resulting spermatozoa pellets and seminal plasma fractions were analyzed for the presence of LOX. Since lanes 1 and 3, lanes 2 and 4, lanes 5 and 7 and lanes 6 and 8 did not appear to differ in band density, it was concluded that the speed at which the samples were centrifuged did not affect the amount of 15-LOX found in sample type (FIG. 5). Bands were present in the lanes with spermatozoa samples (Lanes 3, 5, and 7) in the expected 65-75 kDa range (Lane 1), which typifies 15-LOX molecular weight. Boar 17-2 had a higher density LOX crossreactive band than boar 96-1, suggesting that different boars have different percentages of LOX in their ejaculated spermatozoa. Seminal plasma samples (Lanes 2, 4, 6, and 8) did not contain 15-LOX.

Figure 7:
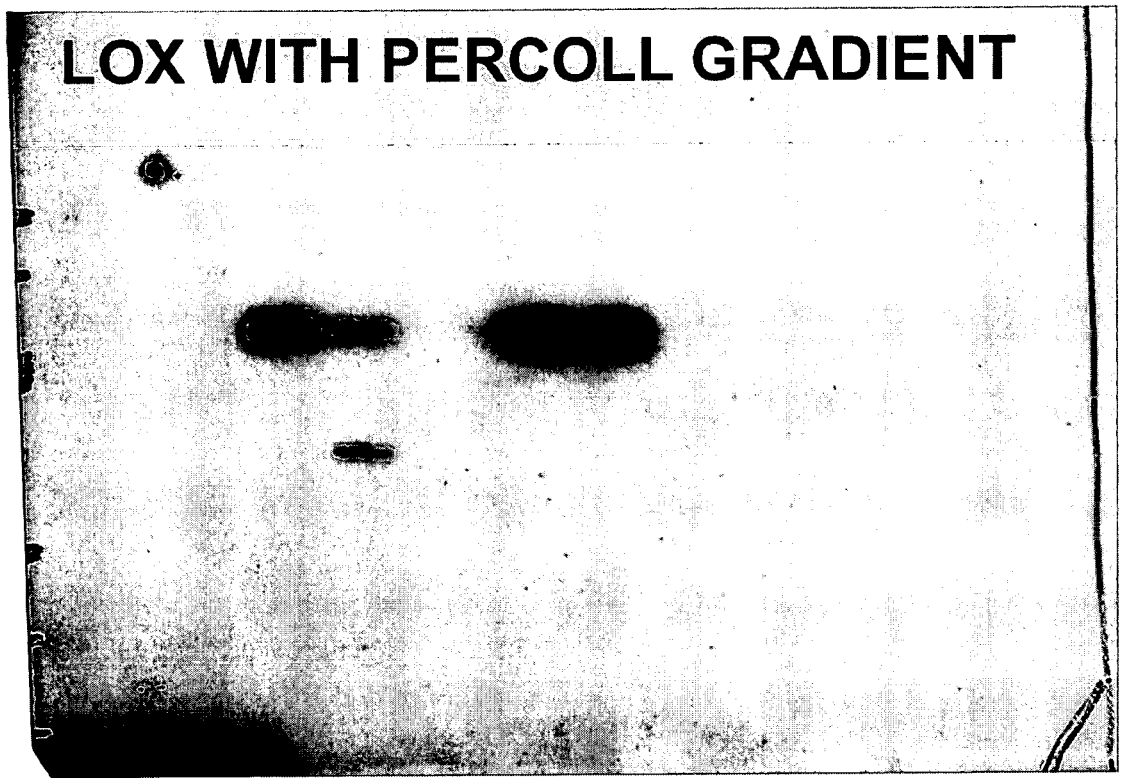
FIG. 7 illustrates an example of Western blot analysis for the presence of 15-LOX in Percoll gradient fractions of ejaculated spermatozoa as evaluated in FIG. 6. Ejaculated spermatozoa from two boars, 17-2 and 96-1, were subjected to a Percoll gradient and divided into three distinct fractions: cellular debris, immotile spermatozoa, and motile spermatozoa. Known molecular weight proteins were used as a marker (lane 1). Analysis of boar 17-2 include cellular debris (lane 2), immotile spermatozoa (lane 3), and motile spermatozoa (lane 4). Analysis of boar 96-1 include cellular debris (lane 5), immotile spermatozoa (lane 6), and motile spermatozoa (lane 7).

Ejaculated spermatozoa from two boars, boar 17-2 and 96-1, were subjected to a Percoll gradient that separated the samples into three distinct layers: a layer of primarily cellular debris (DL) such as CD, epithelial cells, and bacteria; an immotile spermatozoa layer (IL) that contained a large percentage of spermatozoa with CD (FIG. 6); and a motile spermatozoa layer (ML) that contained a large percentage of morphologically normal spermatozoa (FIG. 6). The three separate fractions from each of the two different boars were subjected to Western blot analysis using an antibody to 15-LOX. The DL and IL showed crossreactivity with 15-LOX for both boars while the ML did not crossreact with 15-LOX (FIG. 7). Boar 17-2 had bands at approximately 80-90 kDa for the DL and IL, with the IL having a lower density band. The IL had an additional, lower molecular weight band at 55-70 kDa that was unique to this spermatozoa fraction and boar. Boar 96-1 had similar band density for the DL and IL fractions indicating that 15-LOX expression was similar between the DL and IL fraction.

In this study 15-LOX was strongly crossreactive with the fractions of the Percoll gradient that contained a large percentage of CD, whether they were attached to the spermatozoa in the immotile spermatozoa layer or free CD in the debris layer, indicating that samples with a large percentage of CD may have a strong crossreactivity to 15-LOX. One of the boars, Boar 17-2, had a lower density, lower molecular weight band in the immotile sperm fraction that the other boar, Boar 96-1, did not have. This additional band may represent breakdown products of 15-LOX over time.

Figure 8:
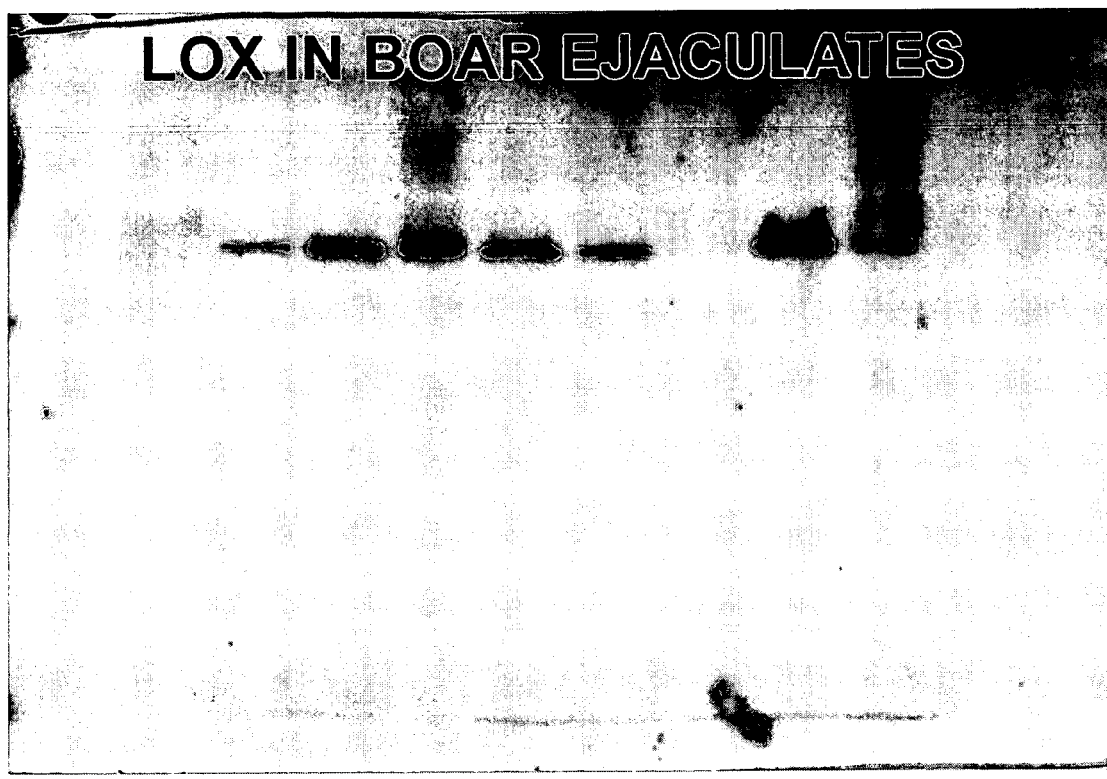
FIG. 8 illustrates an example of Western blot analysis for the presence of 15-LOX in ejaculated boar spermatozoa from different boars. The analysis of ejaculated spermatozoa samples from different boars include boar 96-1 (lane 2), boar 14-1 (lane 3), boar 68-2 (lane 4), boar 17-2 (lane 5), boar 90-4 (lane 6), boar 92-1 (lane 7), a second spermatozoa sample from boar 96-1 (lane 8), and boar 96-4 (lane 9).

Western blot analysis was conducted on ejaculated spermatozoa samples from several different boars. There was differential expression of 15-LOX among the boars represented in the analysis (FIG. 8). All boars except boar 92-1 had 15-LOX crossreactive bands at approximately 75-85 kDa. Boar 96-1, who was represented twice on this analysis, had a higher density band from one ejaculate (Lane 7) than another ejaculate (Lane 1). Thus, different boars or different samples from the same boar may have differential 15-LOX crossreactivity. It was indicated that the differential expression of 15-LOX in these samples was because some samples contained different amounts of CD and, thus, 15-LOX was present in higher abundance in the samples with a higher percentage of spermatozoa with CD. An association of 15-LOX with CD presence and decreased fertility was thus further indicated.

Example 4

Materials and Methods

A. Boar ejaculated sperm samples

Boar ejaculates were obtained by gloved-hand technique from Duroc x Landrace-Yorkshire crossbred boars at the University of Missouri swine farm. Boars were between nine months and two years of age at the time of collection. Samples were collected as needed, with a minimum three-day resting period between ejaculates.

B. Sperm Evaluation

High-resolution differential interference contrast (DIC) light microscopy was used for semen evaluation. Spermatozoa were photographed using the CoolSnap HQ operated by MetaMorph software using a Nikon Eclipse E800 microscope. At least 100 spermatozoa were randomly counted from each sample, evaluated for morphology and classified as having: normal morphology, a proximal CD, a distal CD or non-CD abnormal morphology. Spermatozoa were considered to have a proximal CD if the CD was present at the head-midpiece junction or in the upper 50% of the midpiece region. Spermatozoa were considered to have a distal CD if the CD was present at the midpiece-principal piece junction or in the lower 50% of the midpiece region. Spermatozoa were considered to have abnormal morphology if they were coiled, had misshapen heads, poor head-midpiece connections or other non-CD morphological abnormalities.

C. Sperm Processing

Samples were centrifuged at 500×g (1000×g or 2500×g when specified) for eight minutes. Seminal plasma was frozen at −20° C. and the spermatozoa pellet was divided and part of it was frozen at −20° C. and the other part was fixed in 2% formaldehyde for 40 minutes onto lysine-coated coverslips.

D. Percoll Gradient

A 45%/90% Percoll gradient was made using 2 ml 45% Percoll (1 ml 90% Percoll and 1 ml Sperm TL media with bovine serum albumin) and 2 ml 90% Percoll. The spermatozoa sample obtained was centrifuged at 500×g for eight minutes to form a spermatozoa pellet. One milliliter of the spermatozoa pellet was placed on top of the Percoll gradient and centrifuged for five minutes at 1000×g. Spermatozoa were isolated from the different layers and at least 100 spermatozoa were randomly counted and classified according to parameters established (see Spermatozoa evaluation). Spermatozoa (1 ml of spermatozoa pellet) were washed twice through 8 ml of Sperm TL media with polyvinyl pyrrolidone at 500×g for eight minutes. The spermatozoa pellets were divided and either frozen at −20° C. or fixed onto lysine-coated coverslips (see Spermatozoa processing above).

E. Epididymal and Testicular Spermatozoa

Boars from a commercial boar stud and the University of Missouri's swine herd were euthanized at the University of Missouri Veterinary Diagnostic Laboratory and tissues (testis and caput, corpus, and cauda epididymis) from both the left and right side of the reproductive tract were collected. Spermatozoa samples from tissue sections were obtained by repeated, gentle mincing of the tissue to allow spermatozoa cells to flow into Sperm TL media with polyvinyl pyrrolidone. Spermatozoa were passed through a 105 micron Spectra/Mesh® macroporous filter (Spectrum Medical Industries, Inc., Houston, Tex.) and centrifuged at 500×g for five minutes to form a spermatozoa pellet. The pellet was diluted with Sperm TL media and spermatozoa morphology was assessed using the same parameters as for ejaculated spermatozoa (see Spermatozoa evaluation above). Spermatozoa pellets were divided and either frozen at −20° C. or attached to lysine-coated coverslips using formaldehyde.

F. Antibodies

The primary antibody used was anti-15 lipoxygenase (LOX), rabbit serum raised against YLRPSIVENSVAI (SEQ ID NO:1) peptide of C-terminal domain of rabbit reticulocyte 15-LOX, diluted 1/100 for immunofluorescence or 1/2000 for western blotting. Secondary antibodies used were: goat anti-rabbit FITC (Zymed, San Francisco, Calif., Lot 10665523, diluted 1/80), goat anti-rabbit horseradish peroxidase (GAR-IgG HRP, Zymed, Lot 00962107, diluted 1/10000). Where applicable, DNA was counterstained with DAPI (4',6'-diamidino-2-phenylindole hydrochloride, diluted 1/80).

G. Immunocytochemistry on Sperm Samples

Spermatozoa were permeabilized using Phosphate Buffer Saline (PBS) with 0.1% Triton-100 for 40 minutes and washed in 5% normal goat serum (NGS) in PBS with 0.1% Triton-100. Anti-15-LOX antibody was diluted in 1% NGS in PBS with 0.1% Triton X-100 and added to spermatozoa for 40 minutes. The coverslips were then washed in 1% NGS in PBS with 0.1% Triton X- 100. The secondary antibody, GAR-IgG FITC (Zyrned) and DAPI were added for one hour. Images were acquired using CoolSnap HQ operated by MetaMorph software using a Nikon Eclipse E800 microscope. Images were optimized using Adobe® Photoshop 5.5 (Adobe Systems, Inc., San Jose, Calif.).

H. Tissue Sections

Tissue sections from the left and right testis and caput, corpus and cauda epididymis were cut into 5 mm sections and placed in 4% paraformaldehyde at 4° C. overnight. Tissue sections were washed in 0.1 M PBS for four hours, changing solution every hour. Tissue was stored in 5% sucrose in PBS for 48 hours and placed in 70% ethanol for 20 minutes. Tissue sections were paraffinized, cut into sections and placed on slides by the University of Missouri Histology Laboratory. Slides were placed in xylene for 30 minutes and then placed in 100%, 90% and 70% ethanol for one minute each. Slides were washed in water for 20 minutes and then PBS for five minutes. Slides were incubated in $NH_4Cl$ for 10 minutes and then washed in PBS three times. Slides were steamed in the Flavor Scenter Handy Steamer™ (Black and Decker; Towson, Md.) with citric acid buffer (pH 6.0) for 20 minutes and then washed in PBS with 0.1% Triton-100.

I. Immunocytochemistry on Tissue Sections

Non-specific tissue sights were blocked using 5% NGS in PBS with 0.1% Triton-100 for 25 minutes. Anti-15-LOX antibody was incubated with the slides for two hours. Slides were washed in 1% NGS in PBS with 0.1% Triton-100 and incubated in GAR-IgG FITC and DAPI for one hour. Slides were washed in 1% NGS in PBS with 0.1% Triton-100 and mounted using VectaShield® (Vector Laboratories, Inc., Bulingame, Calif.). Images were acquired using CoolSnap HQ operated by MetaMorph software using a Nikon Eclipse E800 microscope. Images were optimized using Adobe® Photoshop 5.5 (Adobe Systems, Inc.).

J. Colloidal Gold Labeling of Sperm LOX

Spermatozoa pellets were fixed in 2% formaldehyde for 40 minutes and then permeabilized for 40 minutes using PBS with 0.1% Triton x-100. The spermatozoa pellet was blocked using 5% NGS in PBS with 0.1% Triton x-100. Anti-15-LOX antibody was incubated with the spermatozoa overnight at 4° C. Spermatozoa were incubated with GAR IgG conjugated to 12 nm colloidal gold particles for one hour at room temperature with occasional stirring. Spermatozoa were washed in PBS with 0.1% Triton x-100 and centrifuged for 5 minutes at 500×g. Spermatozoa pellets were fixed in a solution of paraformaldehyde, glutaraldehyde, and cacodylate buffer, embedded, and taken to the University of Missouri's Electron Microscopy Core Facility for processing.

K. Western Blots

Sperm proteins were extracted by adding the spermatozoa sample to a solution of extraction buffer containing 50 mM Tris HCl, 20 mM imidazole, 1 mM EDTA, and 5 mM benzamidine HCl (pH 6.0). The spermatozoa solution was ground for three and a half minutes using a pestle attached to a 9.6 volt electric drill (Black and Decker®, Towson, Md., no. CD9600). PMSF, Protease Inhibitor Cocktail (Sigma, St. Louis, Mo., lot #102K41) and Triton x-100 were added to inhibit protein degradation and denature sample proteins. Samples were spun in a cold centrifuge at 4° C. at 16000×g for 60 minutes. To standardize the protein samples, standard Bradford protein estimation using Bio-Rad Protein Assay (Bio-Rad Laboratories, Hercules, Calif.) was done using 595 nm wavelength absorbance. All protein samples were diluted to a final standard protein concentration. To each sample was added 2% SDS, 20% glycerine, 0.05% bromphenol blue, and 5% beta-mercaptoethanol. Samples were boiled for five minutes and then run on 10% Tris-glycine gel (BioWhittaker Molecular Applications, Rockland, Me.) using 19-30 µg protein per sample lane, with all lanes in each gel adjusted to the same protein concentration. Ten microliters of Kaleidoscope Prestained Standards (Bio-Rad Laboratories, Hercules, Calif., Control #95326) were used as the molecular marker. After electrophoresis, proteins were electrophoretically transferred to polyvinylidene fluoride membranes (ImmobilonTM-P Transfer Membranes, Millipore Corp., Bedford, Mass.). Blots were blocked for 17-30 hours using Blocker™ Casein in PBS solution (Pierce, Rockford, Ill., Prod. 37528). Anti-15-LOX antibody (diluted 1/2000) was added to 0.25% Tris Base Saline (TBS)-Tween 20 and then incubated with the membrane for 18-28 hours. Blots were washed three times in 0.25% TBS-Tween 20 and then incubated for one hour in GAR-IgG HRP (Zymed). The membrane was washed three times in 0.25% TBS-Tween and developed using SuperSignal® West Pico Chemiluminescent Substrate (Pierce). The membrane was developed on Kodak BioMax Light Film (Kodak, Cedex, France, lot #2331502) for 0.5-20 minutes using a Kodak M35A X-OMAT Processor (Kodak).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,367,110
U.S. Pat. No. 4,393,075
U.S. Pat. No. 4,452,901
U.S. Pat. No. 4,668,621
U.S. Pat. No. 4,708,964
U.S. Pat. No. 4,761,403
U.S. Pat. No. 5,232,941
U.S. Pat. No. 5,310,959
U.S. Pat. No. 5,326,785
U.S. Pat. No. 5,861,268
U.S. Pat. No. 5,928,654
U.S. Pat. No. 6,099,834
U.S. Pat. No. 6,217,875
U.S. Pat. No. 6,486,181
U.S. Pat. No. 6,541,519
U.S. Pat. No. 6,589,758
U.S. Patent Prov. 60/447,675
Abbondanzo et al., *Breast Cancer Res. Treat.*, 16:182(151), 1990
Allred et al., *Breast Cancer Res. Treat.*, 16:182(149), 1990
Althouse et al., *Theriogenology*, 50:535, 1998.
Brash, *J. Biol. Chem.*, 274:23679, 1999.
Brown et al. *Immunol. Ser.*, 53:69-82, 1990.
Capaldi et al., *Biochem. Biophys. Res. Comm.*, 76:425, 1977.
Cho et al., *J. Med. Chem.*, 34:1503, 1991.
Conrad, *Clin Rev Allergy Immunol.*, 17(1-2):71-89, 1999.
Crowther, In: *Methods in Molecule Biology*, Vol. 42, Humana Press; NJ, 1995
Engvall and Perlmann, *Immunochem.*, 8:871-873, 1971.
Engvall, *Lancet*, 2(8000):1410, 1976.
Engvall, *Med Biol.*, 55(4):193-200, 1977.
Engvall, *Methods Enzymol*, 70(A):419-39, 1980.
Feussner and Wasternack, *Annu. Rev. Plant Biol.*, 53:275, 2002.
Fritsch et al., *Acta Biol. Med. Ger.*, 38:1315, 1979.
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Gripenberg et al., *Scand J Immunol.*, 7(2):151-157, 1978.
Grüllich et al., *FEBS Lett.*, 489:51, 2001.
Hammarström, *Biochem. Biophys. Acta*, 487:517-519, 1977.
Harlow and Lane, In: *Antibodies, a Laboratory Manual*, Cold Spring Harbor Laboratory, pp 139-281, 1988.
Hope et al., *Biochem. Pharmacol.*, 32:367, 1983.
Kimura et al., *Biochem. Biophys. Acta*, 922:278, 1987.
Kliewer et al., *Cell*, 83:813-819, 1995.
Kohler and Milstein, *Eur. J. Immunol.*, 6:511-519, 1976.
Kohler and Milstein, *Nature*, 256:495-497, 1975.
Koshihara et al., *Biochem. Biophys. Acta*, 792:92, 1984.
Kubo et al., *Chem. Pharm. Bull.*, 32:2724, 1987.
Lankin et al., *Biomed. Biochim. Acta*, 44:655, 1985.
Lax et al., *Biochim. Biophys. Acta*, 1043:12, 1990.
Makler et al., *Transfusion*, 21(3):303-312, 1981
Nakamura et al., In: *Handbook of Experimental Immunology* (4th Ed.), Weir et al. (Eds.), 1:27, Blackwell Scientific Publ., Oxford, 1987.
Oliw and Sprecher, *Biochim. Biophys. Acta*, 1002:283, 1989.
Omina and Hammarström et al, *J. Biol. Chem.*, 255:8023, 1980.
PCT Appln. WO 84/03564
Saez et al., *Scand. J. Infect. Dis.*, 35(4):282-4, 2003.
Salari et al., *Prostagland. Leukot. Med.*, 13:53, 1984.
Sarngadharan et al., *Princess Takamatsu Symp.*, 15:301-308, 1984.
Schewe et al., *FEBS Lett.*, 60:149, 1975.
Sekiya and Okuda, et al., *Biochem. Biophys. Res Commun.*, 105:1090, 1982.
Shureiqi et al., *J. Natl. Cancer Inst.*, 92:1136, 2000.
Sutovsky et al. *Reprod. Biomed. Online;* 8(1): 24-34, 2004.
van Leyen et al., *Nature;* 395: 392-395, 1998.
Yamamoto, *Free Radic. Biol. Med.*, 10: 149, 1991.
Yoshimoto et al., *Biochem. Biophys. Acta*, 713:470, 1982.

What is claimed is:

1. A method of evaluating the fertility of a sample of spermatozoa comprising detecting the content and/or activity of 15-lipoxygenase (15-LOX) in the sample, wherein an increased content and/or activity of 15-LOX relative to a control sample is associated with decreased fertility.

2. The method of claim 1, wherein detecting the content and/or activity of 15-LOX comprises evaluating testicular, epididymal, and ejaculated spermatozoa.

3. The method of claim 1, wherein the sample is semen.

4. The method of claim 1, wherein detecting is by immunocytochemistry or electron microscopy utilizing colloidal gold particles.

5. The method of claim 1, wherein detecting is by Western blot analysis.

6. The method of claim 1, wherein the sample of spermatozoa is from a bull, pig, goat, sheep, horse, dog or cat.

7. The method of claim 1, wherein the sample of spermatozoa is from a human.

8. The method of claim 1, wherein said detecting comprises immunologic detection.

9. The method of claim 8, wherein said immunologic detection comprises detection with polyclonal antisera.

10. The method of claim 8, wherein said immunologic detection comprises detection with a monoclonal antibody preparation.

11. The method of claim 8, wherein said immunologic detection comprises ELISA.

12. The method of claim 8, wherein said immunologic detection comprises RIA.

13. The method of claim 8, wherein said immunologic detection comprises Western blot.

14. The method of claim 11, wherein said ELISA is a sandwich ELISA comprising binding of 15-LOX to a first antibody preparation fixed to a substrate and a second antibody preparation labeled with an enzyme.

15. The method of claim 14, wherein said enzyme is alkaline phosphatase or horseradish peroxidase.

16. The method of claim 1, wherein detection comprises detection of mRNA.

17. The method of claim 1, wherein detecting comprises detecting a product and/or substrate of 15-LOX.

18. The method of claim 17, wherein detecting comprises detecting at least a first hydroxyeicosatetraenoic acid (HETE), hydroperoxyeicosatetraenoic acid (HPETE) and/or thiobarbiturate-reactive substance (TBARS).

19. The method of claim 1, further comprising detecting the content and/or activity of 15-LOX in at least two samples of spermatozoa from a subject.

20. The method of claim 1, further defined as comprising evaluating fertility of a plurality of samples of spermatozoa by detecting the content and/or activity of 15-LOX in the samples.

* * * * *

SEQUENCE LISTING

<160> NUMBER OF SEQ ID NOS: 18

<210> SEQ ID NO 1
<211> LENGTH: 13
<212> TYPE: PRT
<213> ORGANISM: Lepus Reticulocyte

<400> SEQUENCE: 1

Tyr Leu Arg Pro Ser Ile Val Glu Asn Ser Val Ala Ile
 1               5                  10

<210> SEQ ID NO 2

```
<211> LENGTH: 13
<212> TYPE: PRT
<213> ORGANISM: Homo sapiens

<400> SEQUENCE: 2

Tyr Leu Arg Pro Ser Val Val Glu Asn Ser Val Ala Ile
1               5                   10

<210> SEQ ID NO 3
<211> LENGTH: 13
<212> TYPE: PRT
<213> ORGANISM: Homo sapiens

<400> SEQUENCE: 3

Tyr Leu Asp Pro Pro Leu Ile Glu Asn Ser Val Ser Ile
1               5                   10

<210> SEQ ID NO 4
<211> LENGTH: 13
<212> TYPE: PRT
<213> ORGANISM: Homo sapiens

<400> SEQUENCE: 4

Tyr Leu Lys Pro Ser Cys Ile Glu Asn Ser Val Thr Ile
1               5                   10

<210> SEQ ID NO 5
<211> LENGTH: 13
<212> TYPE: PRT
<213> ORGANISM: Homo sapiens

<400> SEQUENCE: 5

Tyr Leu Asp Pro Val Leu Ile Glu Asn Ser Ile Ser Ile
1               5                   10

<210> SEQ ID NO 6
<211> LENGTH: 13
<212> TYPE: PRT
<213> ORGANISM: Homo sapiens

<400> SEQUENCE: 6

Tyr Leu Ser Pro Asp Arg Ile Pro Asn Ser Val Ala Ile
1               5                   10

<210> SEQ ID NO 7
<211> LENGTH: 13
<212> TYPE: PRT
<213> ORGANISM: Mus musculus

<400> SEQUENCE: 7

Tyr Leu Arg Pro Ser Leu Val Glu Asn Ser Val Ala Ile
1               5                   10

<210> SEQ ID NO 8
<211> LENGTH: 13
<212> TYPE: PRT
<213> ORGANISM: Mus musculus

<400> SEQUENCE: 8

Tyr Leu Lys Pro Ser Arg Ile Glu Asn Ser Ile Thr Ile
1               5                   10

<210> SEQ ID NO 9
<211> LENGTH: 13
<212> TYPE: PRT
```

```
<213> ORGANISM: Mus musculus

<400> SEQUENCE: 9

Tyr Leu Arg Pro Ser Leu Val Glu Asn Ser Val Thr Ile
 1               5                  10

<210> SEQ ID NO 10
<211> LENGTH: 13
<212> TYPE: PRT
<213> ORGANISM: Mus musculus

<400> SEQUENCE: 10

Tyr Leu Asp Pro Pro Leu Ile Glu Asn Ser Val Ser Ile
 1               5                  10

<210> SEQ ID NO 11
<211> LENGTH: 13
<212> TYPE: PRT
<213> ORGANISM: RAT

<400> SEQUENCE: 11

Tyr Leu Arg Pro Ser Met Val Glu Asn Ser Val Ala Ile
 1               5                  10

<210> SEQ ID NO 12
<211> LENGTH: 13
<212> TYPE: PRT
<213> ORGANISM: RAT

<400> SEQUENCE: 12

Tyr Leu Asp Pro Pro Leu Ile Glu Asn Ser Val Ser Ile
 1               5                  10

<210> SEQ ID NO 13
<211> LENGTH: 13
<212> TYPE: PRT
<213> ORGANISM: RAT

<400> SEQUENCE: 13

Tyr Leu Ser Pro Asp Arg Ile Pro Asn Ser Val Ala Ile
 1               5                  10

<210> SEQ ID NO 14
<211> LENGTH: 10
<212> TYPE: PRT
<213> ORGANISM: RAT

<400> SEQUENCE: 14

Tyr Leu Ser Pro Asp Arg Phe Gln Thr Val
 1               5                  10

<210> SEQ ID NO 15
<211> LENGTH: 13
<212> TYPE: PRT
<213> ORGANISM: Bovillus

<400> SEQUENCE: 15

Tyr Leu Arg Pro Ser Leu Val Glu Asn Ser Val Ala Ile
 1               5                  10

<210> SEQ ID NO 16
<211> LENGTH: 13
<212> TYPE: PRT
<213> ORGANISM: Bovillus
```

```
-continued

<400> SEQUENCE: 16

Tyr Leu Asp Pro Pro Leu Ile Glu Asn Ser Val Ser Ile
  1               5                  10

<210> SEQ ID NO 17
<211> LENGTH: 13
<212> TYPE: PRT
<213> ORGANISM: Porcarius

<400> SEQUENCE: 17

Tyr Leu Arg Pro Ser Arg Val Glu Asn Ser Val Ala Ile
  1               5                  10

<210> SEQ ID NO 18
<211> LENGTH: 13
<212> TYPE: PRT
<213> ORGANISM: Porcarius

<400> SEQUENCE: 18

Tyr Leu Arg Pro Ser Ser Val Glu Asn Ser Val Ala Ile
  1               5                  10
```